(12) United States Patent
Ninomiya et al.

(10) Patent No.: US 8,662,133 B2
(45) Date of Patent: Mar. 4, 2014

(54) ULTRASONIC PROCESSING APPARATUS

(75) Inventors: Akihide Ninomiya, Kanonji (JP);
Kazuo Ukegawa, Kanonji (JP); Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 13/823,391

(22) PCT Filed: Sep. 6, 2011

(86) PCT No.: PCT/JP2011/070282
§ 371 (c)(1),
(2), (4) Date: Mar. 14, 2013

(87) PCT Pub. No.: WO2012/043171
PCT Pub. Date: Apr. 5, 2012

(65) Prior Publication Data
US 2013/0167629 A1    Jul. 4, 2013

(30) Foreign Application Priority Data
Sep. 30, 2010 (JP) .................................. 2010-223074

(51) Int. Cl.
*B32B 37/00* (2006.01)
(52) U.S. Cl.
USPC .................... 156/580.2; 156/555; 156/580.1
(58) Field of Classification Search
USPC ................. 156/73.1, 555, 580.1, 580.2, 582, 156/583.1; 264/442, 443, 444, 445; 425/174.2
See application file for complete search history.

(56) References Cited

U.S. PATENT DOCUMENTS

| | | | | |
|---|---|---|---|---|
| 5,552,013 | A | * | 9/1996 | Ehlert et al. .................. 156/555 |
| 6,120,629 | A | * | 9/2000 | Shannon et al. ............. 156/73.1 |
| 7,341,084 | B2 | * | 3/2008 | Van Eperen .................. 156/510 |
| 7,374,627 | B2 | * | 5/2008 | McCabe ...................... 156/73.1 |
| 7,704,341 | B2 | * | 4/2010 | Topolkaraev et al. ....... 156/73.1 |
| 7,708,849 | B2 | * | 5/2010 | McCabe ...................... 156/73.1 |
| 2005/0145317 | A1 | | 7/2005 | Yamamoto |
| 2010/0116409 | A1 | | 5/2010 | Yamamoto |

FOREIGN PATENT DOCUMENTS

| | | |
|---|---|---|
| EP | 0084903 A2 | 8/1983 |
| JP | 5839836 U | 3/1983 |
| JP | 58171957 A | 10/1983 |
| JP | 69927 U | 2/1994 |
| JP | 10513128 A | 12/1998 |
| JP | 2004298413 A | 10/2004 |
| JP | 2010115283 A | 5/2010 |

OTHER PUBLICATIONS

PCT/JP2011/070282 International Search Report dated Oct. 4, 2011, with English translation.

* cited by examiner

*Primary Examiner* — James Sells
(74) *Attorney, Agent, or Firm* — Lowe Hauptman & Ham, LLP

(57) ABSTRACT

In a ultrasonic processing apparatus, upstream conveyor and downstream conveyor allow a fibrous web to run in a machine direction continuously. Between the conveyors, a working surface of a first mechanical element serving as a stationary element of the ultrasonic processing apparatus extends diagonally with respect to the machine direction. The fibrous web runs in the machine direction above the working surface. The ultrasonic processing apparatus includes a second mechanical element adapted to move in a direction diagonally intersecting the machine direction. The working surface of the first mechanical element cooperates with the second mechanical element to subject the fibrous web to ultrasonic processing. One of an ultrasonic horn and an anvil is used as the first mechanical element and a remainder of the ultrasonic horn and the anvil is used as the second mechanical element.

8 Claims, 7 Drawing Sheets

ULTRASONIC PROCESSING APPARATUS

RELATED APPLICATIONS

The present application is a National Phase of PCT/JP2011/070282, filed Sep. 6, 2011, and is based on, and claims priority from, Japanese Application No. 2010-223074, filed Sep. 30, 2010.

TECHNICAL FIELD

The present invention relates to ultrasonic processing apparatuses for ultrasonically processing a fibrous web continuously running in a machine direction.

BACKGROUND

There are known ultrasonic processing apparatuses adapted to make a nonwoven fabric containing thermoplastic synthetic fibers or a film of thermoplastic synthetic resin run in the form of a fibrous web in a machine direction and to ultrasonically process such a web in the course of running.

For example, JP S58-39836 U (PTL 1) discloses an ultrasonic processing apparatus including a processing horn energized by ultrasonic oscillations and a pressure roller cooperating with the processing horn. The processing horn and the pressure roller rotationally cooperate with each other to subject a workpiece to ultrasonic processing so that the workpiece may be continuously sealed.

A rotational sealing system disclosed in JP H10-513128 A (PTL 2) includes a drum rotating in a direction in which a workpiece in the form of a fibrous web runs, a first thermal energy input device extending in a cross direction with respect to the rotational direction of the drum and a second thermal energy input device operatively associated with the drum so as to rotate together with the drum and simultaneously to be movable in the cross direction wherein the workpiece is located between the first thermal energy input device and the second thermal energy input device. The second thermal energy input device moves in the cross direction in combination with the first thermal energy input device to impart the workpiece thermal energy in the course of rotation of the drum and, upon completion of thermal energy input, moves away from the first thermal energy input device to its initial position. One of the first and second thermal energy input devices is an ultrasonically oscillating horn and a remainder is an anvil.

CITATION LIST

Patent Literature

{PTL 1} JP S58-39836 U
{PTL 2} JP H10-513128 A

SUMMARY OF INVENTION

Technical Problem

In the ultrasonic processing apparatus disclosed in PTL 1, the ultrasonically processed zone is formed on a fibrous web extends in parallel to the machine direction, and the ultrasonically processed zone extending in the cross direction with respect to the machine direction should not be obtained.

In the rotational sealing system disclosed in PTL 2, it is possible to obtain the ultrasonically processed zone in the form of a sealed zone extending in the cross direction with respect to the workpiece running in the machine direction. In this rotational sealing system, the second thermal energy input device arranged outside the drum rotates together with the drum and simultaneously moves in the cross direction with respect to the rotational direction of the drum to impart the thermal energy to the fibrous web. It is desirable for the second thermal energy input device to complete its operation of thermal energy impartation within an angular range in which the fibrous web winds itself around the drum. In other words, the second thermal energy input device must complete its operation within a time frame defined between a time point at which the fibrous web comes in contact with the drum and a time point at which the fibrous web leaves the drum. If it is desired to repeat such operation at relatively short intervals on the fibrous web running at a high velocity, a plurality of, for example, three to four or more sets of the first and second thermal energy input devices should be operatively associated with the drum, and should complicate the ultrasonic processing apparatus, increase the cost required to manufacture the ultrasonic processing apparatus and make the maintenance management intricate.

An object of this invention is to provide an ultrasonic processing apparatus improved so as to avoid these problems in prior art when subjecting a fibrous web to ultrasonic processing in its width direction.

Solution to Problem

According to this invention, there is provided an ultrasonic processing apparatus including an ultrasonic processing unit for subjecting a fibrous web to ultrasonic processing by interposing the fibrous web between a horn connected with an ultrasonic oscillator and an anvil opposed to the horn.

In the present invention, the ultrasonic processing apparatus includes upstream side conveying means and downstream side conveying means allowing the fibrous web to run in a machine direction continuously. Between the upstream side conveying means and the downstream side conveying means, the ultrasonic processing unit including a first mechanical element defined by one of the horn and the anvil and a second mechanical element defined by a remainder is located in a face to face relation so that the fibrous web is nipped therebetween. The first mechanical element is a stationary element in the ultrasonic processing apparatus being movable neither in the machine direction nor in a cross direction with respect to the machine direction and having a working surface opposed to the second element. The second mechanical element is a movable element adapted to rotate in the cross direction and at the same time to repeat back-and-forth movement between the machine direction and the cross direction across the fibrous web wherein, in the course of moving forward, the movable element is kept in contact with the fibrous web running in the machine direction and cooperates with the working surface of the first mechanical element to subject the fibrous web to the ultrasonic processing and, in the course of moving back, the movable element is spaced away from the fibrous web.

According to one embodiment of the invention, the working surface of the first mechanical element extends in parallel to the direction in which the second mechanical element repeats the back-and-forth movement.

According to another embodiment of the invention, the first mechanical element is defined by a horn and the second mechanical element is defined by a roller-like anvil.

According to still another embodiment of the invention, the first mechanical element is defined by an anvil and the second mechanical element is defined by a roller-like horn.

According to yet another embodiment of the invention, the fibrous web includes two or more fibrous webs interposed between the first mechanical element and the second mechanical element, and the first mechanical element and the second mechanical element are adapted to seal these two or more fibrous webs together.

According to further another embodiment of the invention, the first mechanical element and the second mechanical element partially fuse and cut the fibrous web in a direction in which the second mechanical element repeats the back-and-forth movement.

According to additional embodiment of the invention, the anvil is at least one of heatable type and coolable type.

According to still another embodiment of the invention, the fibrous web includes a web of contiguous diapers wherein the ultrasonic processing is applied to predetermined cutting lines of the web to be cut into individual diapers.

Advantageous Effects of Invention

In the ultrasonic processing apparatus according to this invention, the upstream side conveying means and the downstream side conveying means serve to make the fibrous web run in the machine direction continuously. Between these two means, the working surface of the first mechanical element defining the stationary element in this ultrasonic processing apparatus extends in the direction diagonally intersecting the machine direction. The fibrous web running in the machine direction is subjected, in the course of running in the machine direction, to the ultrasonic processing by cooperation between the second mechanical element being opposed to the working surface and moving in the direction diagonally intersecting the machine direction and the working surface. In such an ultrasonic processing apparatus, the first mechanical element is stationary and the second mechanical element repetitively moves back-and-forward in the direction diagonally crossing the machine direction. Such a simplified structure of the ultrasonic processing apparatus advantageously reduces its manufacturing cost and eases the burden of maintenance.

DESCRIPTION OF EMBODIMENTS

Details of the ultrasonic processing apparatus according to this invention will be more fully understood with reference to the accompanying drawings.

Figure 1:
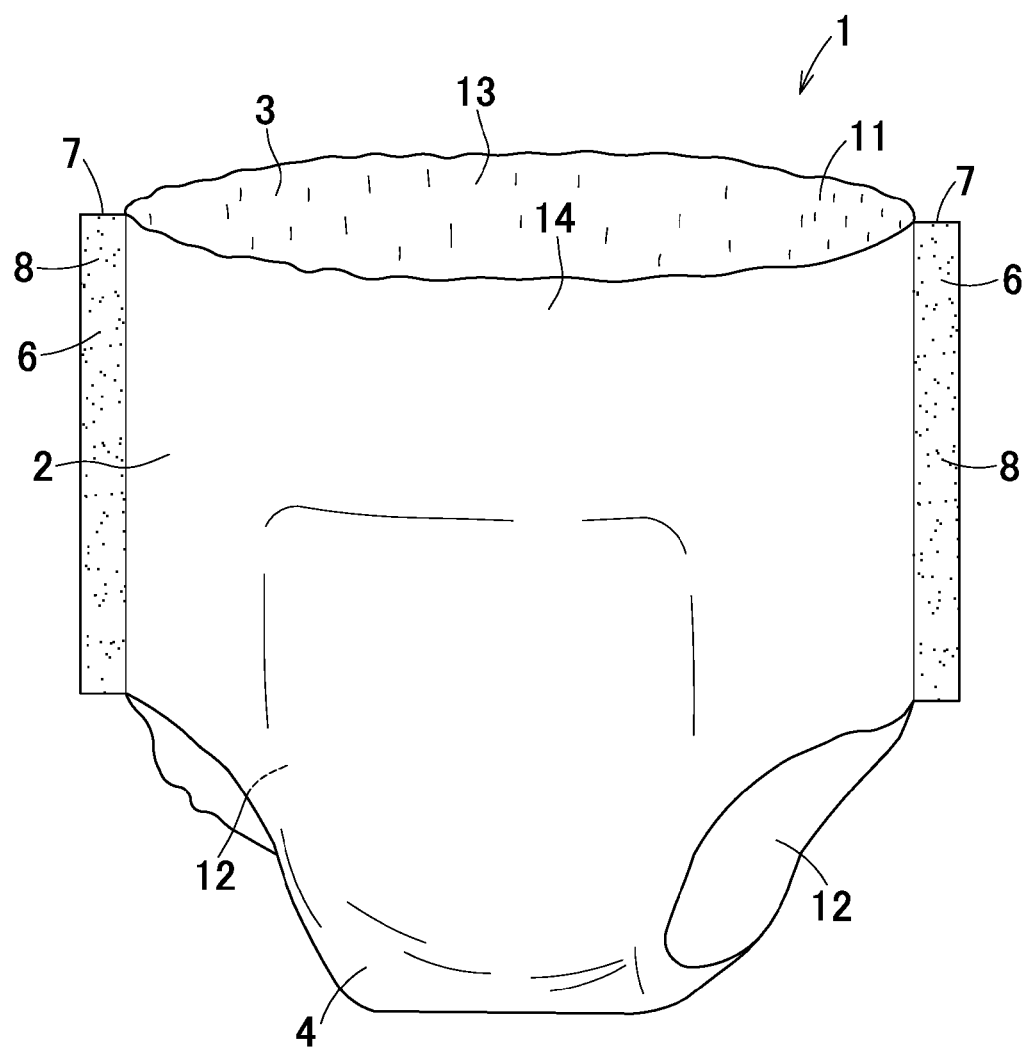
FIG. 1 is a perspective view of a disposable diaper.

Referring to FIG. 1, it is a perspective view of a disposable pants-type diaper 1 to which the ultrasonic processing apparatus is applied (hereinafter described). The diaper 1 includes a front waist region 2, a rear waist region 3 and a crotch region 4 wherein the front waist region 2 and the rear waist region 3 are put flat along respective opposite side edges 6, 7 and joined to each other at a series of seams 8 whereupon the diaper 1 is formed with a waist-opening 11 and leg-openings 12. The waist-opening 11 and the leg-openings 12 are provided along respective peripheral edges with elastics (not shown) attached under tension so that the respective peripheral edges may elastically contract. In the front waist region 2, the rear waist region 3 and the crotch region 4, an inner sheet 13 put in contact with the wearer's skin is formed of a liquid-pervious nonwoven fabric made of thermoplastic synthetic fibers and an outer sheet 14 put in contact with the wearer's garment is formed of a laminate sheet of liquid-impervious film made of a thermoplastic synthetic resin and a nonwoven fabric of thermoplastic synthetic fibers and joined to the outer surface of the film. While the diaper 1 includes also an absorbent structure of known art adapted to be interposed between the inner and outer sheets 13, 14, this absorbent structure is not shown for convenience of illustration.

The seams 8 in such diaper 1 are provided by laying the side edges 6 of the front waist region 2 on the side edges 7 of the rear waist region 3 to overlap with each other and then ultrasonically processing these side edges 6, 7 (described later). More specifically, the seams 8 are provided by laying the inner and outer sheets 13, 14 defining the front waist region 2 on the inner and outer sheets 13, 14 defining the rear waist region 3 and ultrasonically processing these sheets.

Figure 2:
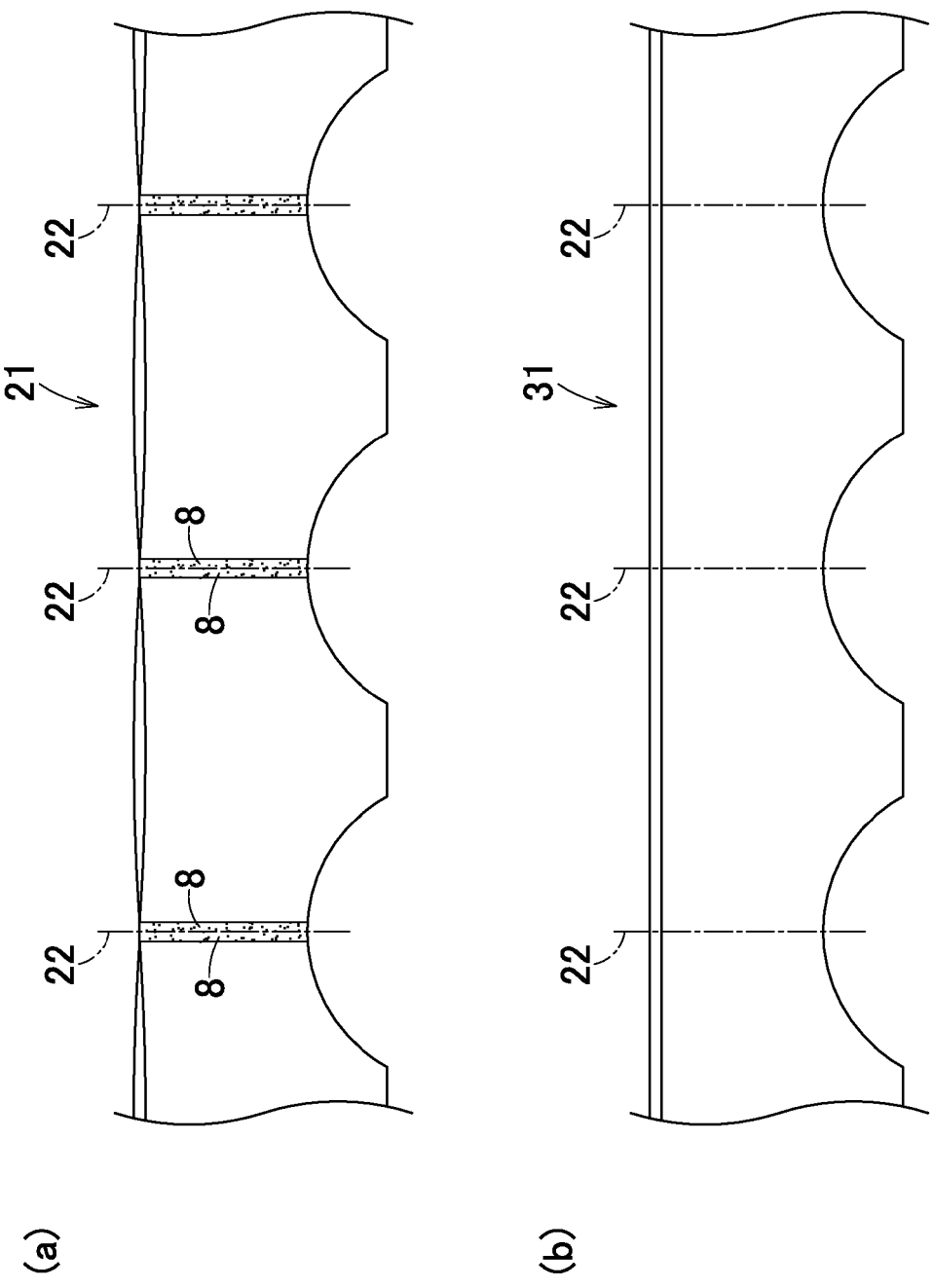
FIG. 2(a) is a web of individual disposable diapers as shown in FIG. 1 being contiguous to one another.
FIG. 2(b) is a fibrous web used to obtain the web of contiguous diaper as illustrated in FIG. 2(a).

Referring to FIG. 2(a), it is a partial perspective view of a web of contiguous diapers 21 including a plurality of the diapers 1 in FIG. 1 contiguously arranged in a longitudinal direction and referring to FIG. 2(b), shown is a partial perspective view of a fibrous web 31 used to make the web of contiguous diapers 21.

The web of contiguous diapers 21 shown in FIG. 2(a) has a plurality of preset cutting lines 22 extending in a width direction and arranged in a longitudinal direction at regular intervals. On both sides of the respective preset cutting lines, each pair of seams 8 shown in FIG. 1 is provided so as to be contiguous with each other. The diaper 1 of FIG. 1 may be obtained by cutting such web of contiguous diapers 21 along the preset cutting lines 22. In FIG. 2(b) showing the fibrous web 31, only the preset cutting lines 22 in FIG. 2(a) are indicated and the seams 8 are still not provided. The fibrous web 31 may be ultrasonically processed to provide the fibrous web 31 with the seams 8 and whereby the web of contiguous diapers 21 shown in FIG. 2(a) is obtained.

Figure 3:
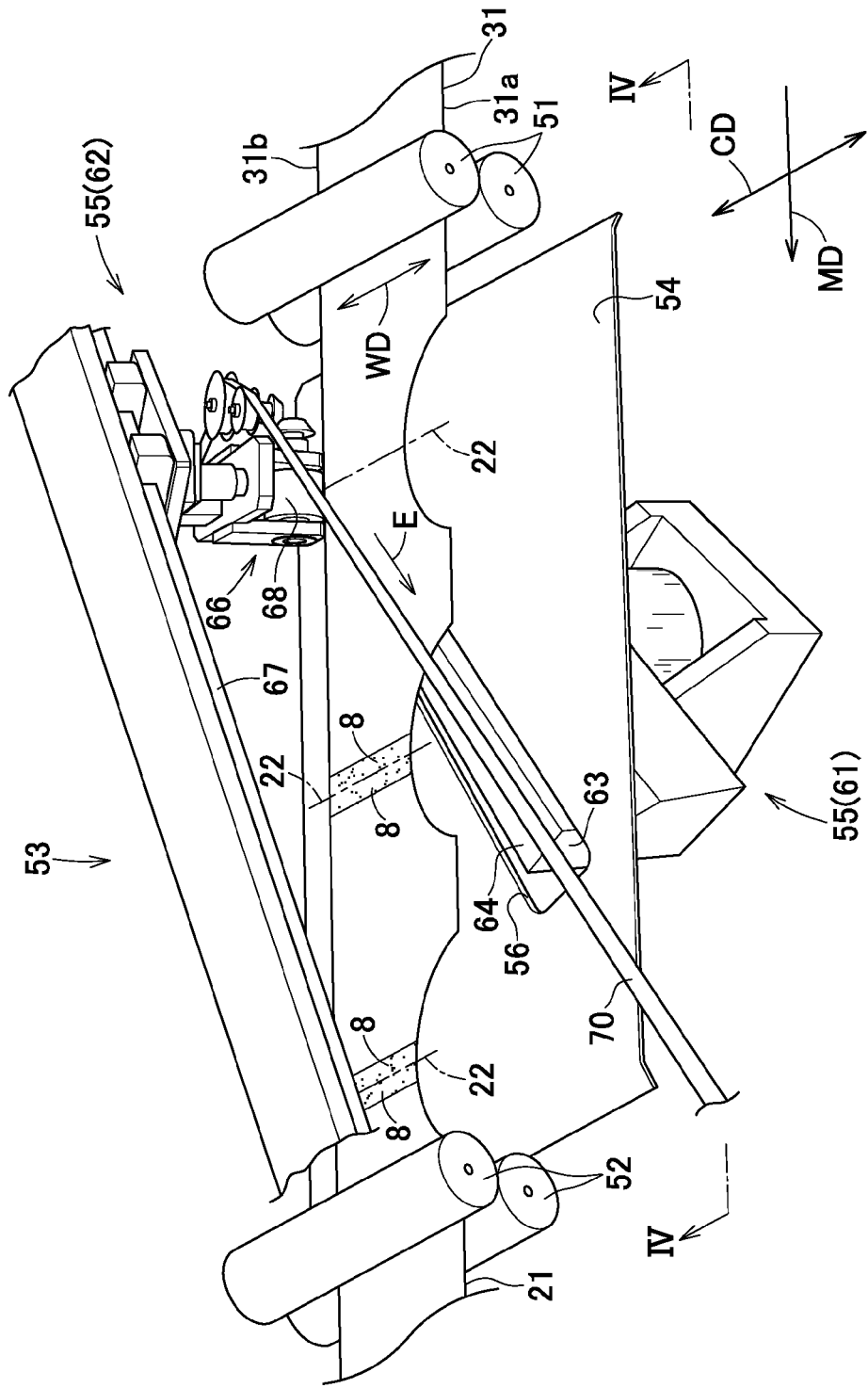
FIG. 3 is a perspective view of an ultrasonic processing apparatus.

Referring to FIG. 3, it is a partial perspective view of an ultrasonic processing apparatus 53 being used to subject the fibrous web 31 shown in FIG. 2(b) to ultrasonic processing, thereby obtaining the web of contiguous diapers 21 shown in FIG. 2(a), wherein a machine direction is denoted by MD and a cross direction being orthogonal to the machine direction MD is denoted by CD. The ultrasonic processing apparatus 53 includes an ultrasonic processing unit 55 interposed between a pair of first conveying rolls 51 located on the upstream side in the machine direction MD and a pair of second conveying rolls 52 located on the downstream side in the machine direction MD. The fibrous web 31 continuously runs from the first conveying rolls 51 toward the second conveying rolls 52 and passes through the ultrasonic processing apparatus 53 in the course of running.

The ultrasonic processing apparatus 53 includes a flat table 54 set between the first conveying rolls 51 and the second conveying rolls 52 and an ultrasonic processing unit 55 composed of two elements opposed to each other across the table 54. Specifically, the ultrasonic processing unit 55 includes a first mechanical element 61 located above or below the table 54 so as to be immovable in the machine direction MD as well as in the cross direction CD and a second mechanical element 62 located to be opposed to the first mechanical element 61 across the table 54 and to be movable diagonally with respect to the machine direction MD. The fibrous web 31 runs above and in parallel to the table 54. In the exemplified embodiment, the first mechanical element 61 is an ultrasonic horn 63 located below the table 54 and a working surface 64 thereof is seen in an elongated opening 56 of the table 54. The opening 56 and the working surface 64 extend diagonally with respect to the machine direction MD. The second mechanical element 62 in the exemplified embodiment is an anvil assembly 66. The anvil assembly 66 is driven by a steel belt 70 to slidably move on a linear slide 67 extending in parallel to the working surface 64 of the ultrasonic horn 63, thereby moving back-and-forth diagonally with respect to the machine direction MD. As will be apparent from FIG. 3, the cross direction CD which is orthogonal to the machine direction MD corresponds to a width direction WD of the fibrous web 31. Therefore, based on the assumption that the fibrous web 31 remains stationary, the anvil assembly 66 can be considered to move back-and-forth diagonally with respect to the fibrous web 31.

A roller-like anvil 68 of the anvil assembly 66 may cooperate with the working surface 64 of the ultrasonic horn 63 to ultrasonically process the fibrous web 31 interposed between the roller-like anvil 68 and the working surface 64 as the reciprocating anvil assembly 66 moves in a forward movement direction indicated by an arrow E.

Figure 4:
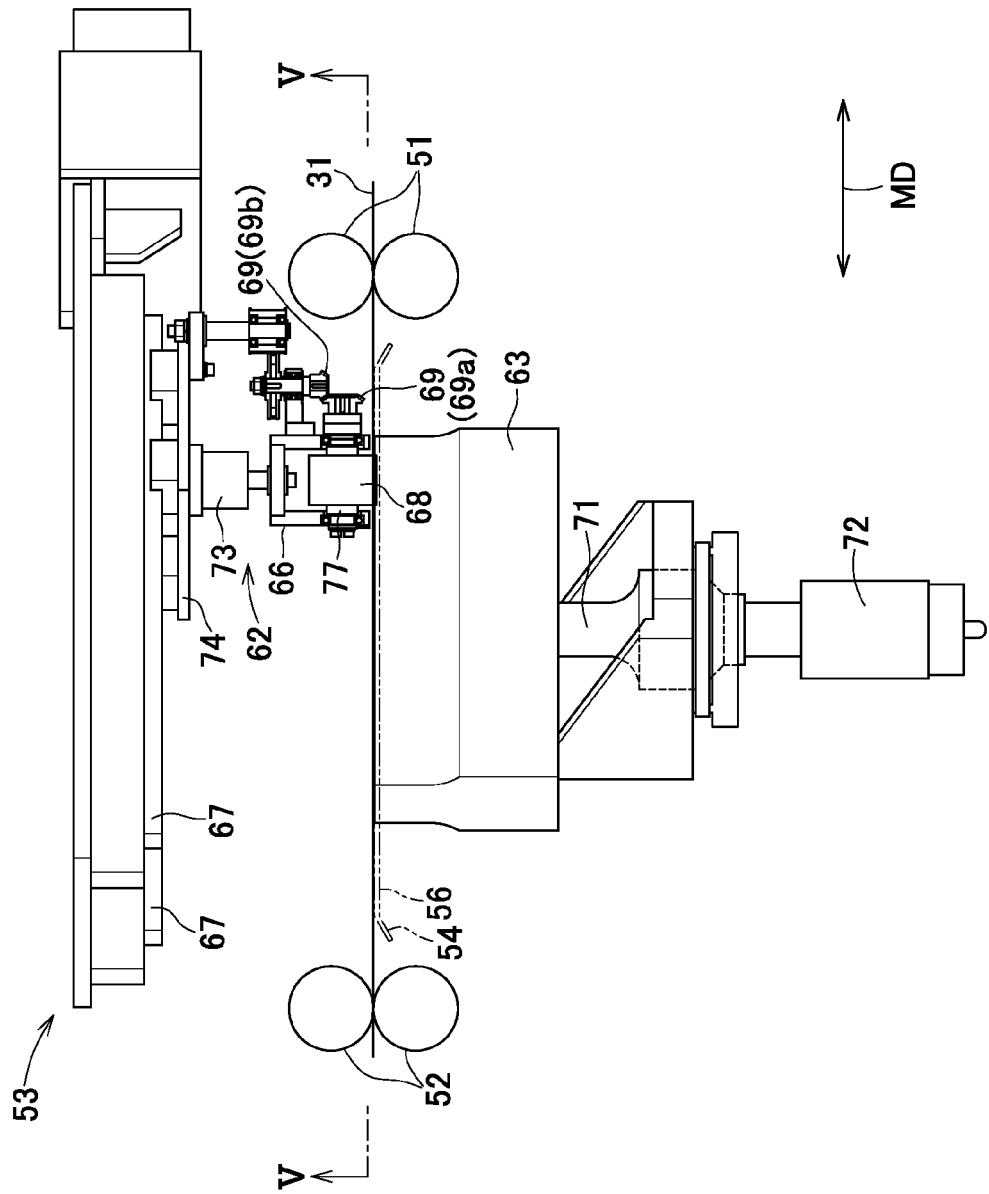
FIG. 4 is a view of the ultrasonic processing apparatus shown in FIG. 3 as viewed in a direction of arrows IV-IV in FIG. 3.

Referring to FIG. 4, it is a view of the ultrasonic processing apparatus 53 shown in FIG. 3 as viewed in the cross direction CD particularly in a direction of arrows IV-IV in FIG. 3, wherein the steel belt 70 is not shown for convenience of illustration. A position of the opening 56 of the table 54 in the ultrasonic processing apparatus 53 is indicated by an imaginary line. The fibrous web 31 continuously runs above the table 54 from the upstream side toward the downstream side in the machine direction MD. The opening 56 is formed so as to intersect diagonally with the fibrous web 31 and to extend outwardly beyond opposite side edges 31a, 31b of the fibrous web 31 (See FIG. 3).

The horn 63 located below the table 54 is connected via an ultrasonic booster 71 to an ultrasonic converter 72 and an ultrasonic oscillator (not shown) so that the horn 63 may be ultrasonically oscillated in a vertical direction as viewed in FIG. 4 by high-frequency power supplied from the ultrasonic oscillator.

The second mechanical element 62 located below the table 54 includes the anvil assembly 66, a bevel gear 69 functioning to rotate the roller-like anvil 68 in the anvil assembly 66, an air cylinder 73 functions to move the roller-like anvil 69 in the vertical direction so that the roller-like anvil 68 may move closer to and apart from the horn 63 and a slide base 74 carrying these components 66, 69, 73 attached thereto and adapted to slide on the linear slide rail 67 in the direction indicated by the arrow E (See FIG. 3) and in its opposite direction. When the roller-like anvil 68 moved downward under the action of the air cylinder 73 and cooperates with the working surface 64 of the horn 63 to nip the fibrous web 31 therebetween, the thermoplastic synthetic resin contained in the fibrous web 31 is fused and the sheets put flat in the fibrous web 31 are sealed together under the effect of ultrasonic oscillations of the working surface 64.

The slide base 74 is adapted to slidably move forward in the direction of the arrow E and to slidably move backward in the opposite direction on the linear slide rail 67 under the action of a servomotor 76 described later in more detail. As long as the slide base 74 is moving forward, processing of the fibrous web 31 to form the seams 8 in FIG. 2(a) is continued. When the slide base 74 has moved forward by a predetermined span, the operation to form the seams 8 is terminated. Thereupon, the roller-like anvil 68 is moved upward apart from the horn 63 and the cooperation of the roller-like anvil 68 with the horn 68 is released. The roller-like anvil 68 having moved upward now reprocesses together with the slide base 74 to a predetermined position and thereupon the roller-like anvil 68 moves again downward under the action of the air cylinder 73 and cooperates again with the horn 63.

The roller-like anvil 68 having such function is adapted to rotate together with a shaft 77 in the cross direction CD (See FIG. 3) with respect to the machine direction MD wherein the shaft 77 extends in the machine direction MD and is coupled to a bevel gear 69a of paired bevel gears 69. The paired bevel gears 69 are adapted to rotate in response to the back-and-forth movement the slide base 74 attached to the anvil assembly 66 as will be described later in more detail.

Figure 5:
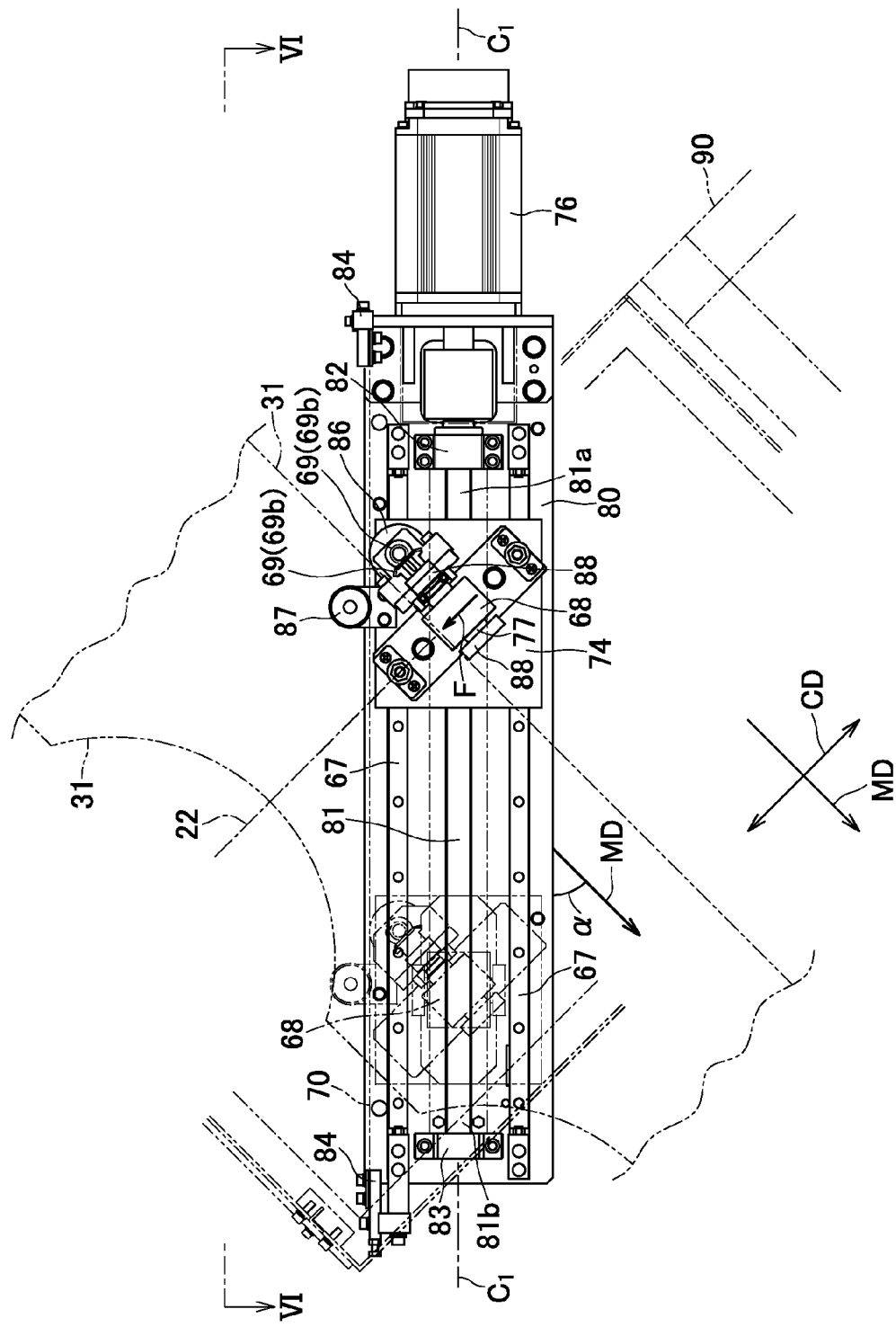
FIG. 5 is a view of the ultrasonic processing apparatus as viewed in a direction of arrows V-V in FIG. 4.

Referring to FIG. 5, it is a view of the ultrasonic processing apparatus 53 as viewed in a direction of arrows V-V in FIG. 4, wherein the ultrasonic processing apparatus 53 is shown as has been appropriately turned around so that the linear slide rails 67 may horizontally extend. In FIG. 5, the fibrous web 31 is indicated by an imaginary line and the steel belt 70 not illustrated in FIG. 4 is also indicated herein by an imaginary line. The slide base 74 to which the anvil assembly 66 is attached by the intermediary of the air cylinder 73 (See FIG. 4) is slidably kept in contact with a pair of parallel linear slide rails 67 attached to a base plate 80. The linear slide rails 67 diagonally intersect with the machine direction at angle α (alpha) in a range of 0 to 90° and diagonally extend across the fibrous web 31. A male ball screw 81 extends in parallel to and between the paired linear slide rails 67 wherein one end 81a of the male ball screw 81 is coupled to the servomotor 76 via a coupling 82 and a remainder end 81b is rotatably supported by a bearing 83 attached to the base plate 80. An imaginary line $C_1$ indicates a rotation center of the ball screw 81. The steel belt 70 indicated by an imaginary line extends in parallel to the linear slide rails 67 and opposite ends thereof are secured to respective support rods 84 which are, in turn, secured to the base plate 80.

In the slide base 74 shown in FIG. 5, the shaft 77 of the roller-like anvil 68 is connected to the one bevel gear 69a of the paired bevel gears 69 and a remainder bevel gear 69b includes a magnetic pulley 86 kept in contact with the steel belt 70. A pressure pulley 87 presses against the steel belt 70 to keep this in a state of tension. The shaft 77 is rotatably supported by a pair of support plates 88. Referring to FIG. 5, in response to rotation of the servomotor 76, the roller-like anvil 68 moves together with the slide base 74 to the position of the roller-like anvil 68 indicated by an imaginary line at which the roller-like anvil 68 can complete the operation of ultrasonic processing. A frame structure 90 partially shown in an imaginary line in FIG. 5 is used to secure the ultrasonic processing apparatus. The respective elements of the ultrasonic processing apparatus exemplarily shown in FIG. 4 may be used by attaching them to the frame structure 90.

Figure 6:
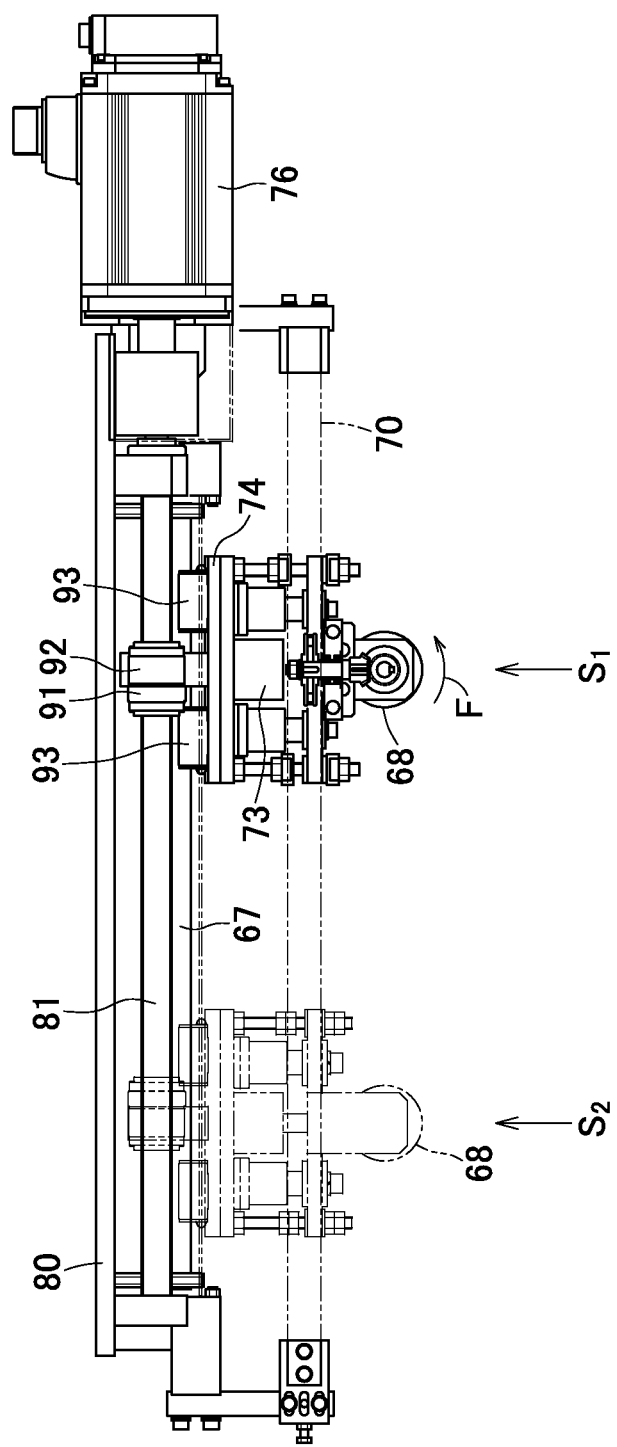
FIG. 6 is a view of the ultrasonic processing apparatus as viewed in a direction of arrows VI-VI in FIG. 5.

Referring to FIG. 6, it is a view of the ultrasonic processing apparatus as viewed in a direction of arrows VI-VI in FIG. 5. In FIG. 6, a female ball screw 91 is engaged with the horizontally extending male ball screw 81 below the base plate 80 horizontally extending. The female ball screw 91 is attached to the slide base 74 by means of securing means 92. The slide base 74 is provided at its four corners with slide guides 93, respectively, which are adapted to interlock with the linear slide rails 67 from below (See FIG. 4). With such an arrangement, the rotational direction of the servomotor 76 may be switched over to move the slide base 74 together with the roller-like anvil 68 back-and-forth between the backward movement limit position $S_1$ and the forward movement limit position $S_2$. The backward movement limits position $S_1$ and the forward movement limit position $S_2$ can be set by a limit switch (not shown) provided in the vicinity of the linear slide rails 67 and the rotational direction of the servomotor 76 can be switched over by electric signal from this limit switch. It is also possible to actuate the air cylinder 73 by the electric signal from the limit switch. For example, when the slide base 74 reaches the backward movement limit position $S_1$, the air cylinder 73 may be actuated to move the roller-like anvil 68 downward, thereby putting the fibrous web 31 in close contact with the roller-like anvil 68 and with the working surface 64 of the ultrasonically oscillating horn 63. In this manner, the zone in the fibrous web 31 put in contact with the roller-like anvil 68 and the working surface 64 of the horn 63 is subjected to ultrasonic processing. Reversely, when the slide base 74 reaches the forward movement limit position $S_2$, the air cylinder 73 may be actuated to move the roller-like anvil 68 apart from the working surface 64, thereby finishing the cooperative operation of the roller-like anvil 68 and the working surface 64 upon the fibrous web 31.

In response to forward movement or backward movement of the slide base 74 in this manner, the magnetic pulley 86 attached to the bevel gear 69b comes in contact with the steel belt 70 and is rotated thereby. Rotation of the magnetic pulley 86 is transmitted via the bevel gear 69b to the bevel gear 69a to rotate the shaft 77 and further to rotate the roller-like anvil 68 in a direction indicated an arrow F (See FIGS. 5 and 6). In consequence, the roller-like anvil 68 rotates in the direction indicated by the arrow F and simultaneously moves forward in the direction indicated by the arrow E to form the fibrous web 31 with the seams 8.

In the ultrasonic processing apparatus 53 having the construction described hereinabove, when it is desired to form the fibrous web 31 continuously running in the machine direction MD at a given velocity with the seams 8 linearly extending across the fibrous web 31, for example, in the direction orthogonal to the machine direction MD as exemplified in FIG. 3, a crossing angle between the direction E in which the roller-like anvil 68 linearly moves forward at a given velocity and the machine direction MD in which the fibrous web 31 runs, i.e., a crossing angle α between the linear slide rails 67 and the machine direction MD is determined on the basis of a velocity at which the roller-like anvil 68 moves forward and a velocity at which the fibrous web 31 runs.

In the ultrasonic processing apparatus 53 according to this invention, the first mechanical element exemplified in the form of the horn 63 is stationary and the second mechanical element exemplified in the form of the anvil 68 repetitively moves back-and-forward in the direction diagonally crossing the machine direction MD at the angle α. Such a simplified structure of the ultrasonic processing apparatus 53 advantageously reduces its manufacturing cost and eases the burden of maintenance.

Figure 7:
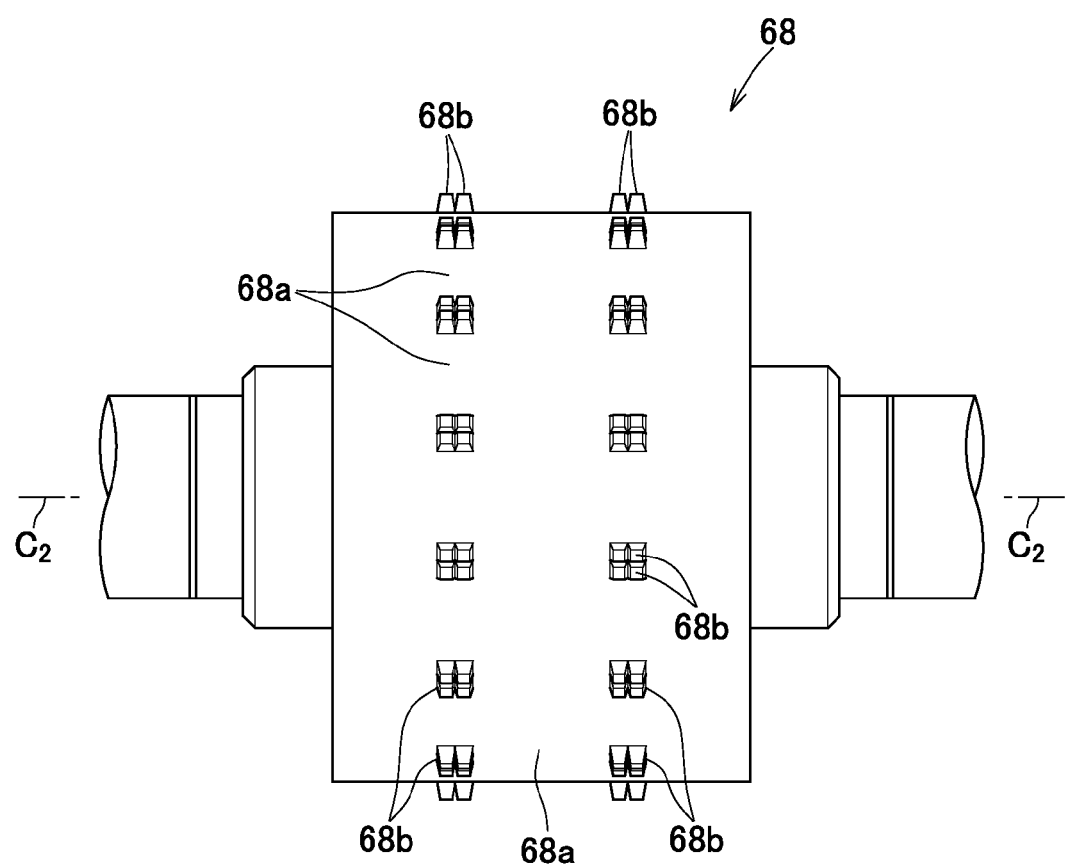
FIG. 7 is a diagram showing an example of a configuration of the anvil's peripheral surface.

Referring to FIG. 7, it is a diagram exemplifying a peripheral surface of the roller-like anvil 68 which can be used in the ultrasonic processing apparatus 53 according to this invention. When the peripheral surface of the roller-like anvil 68 is provided with concave portions 68a and convex portions 68b alternating in a circumferential direction as shown in FIG. 7 as an example, inverted patterns of these concave portions 68a and convex portions 68b may be formed on the seal region 8. Specifically, the concave portions 68a on the peripheral surface reappear on the fibrous web 31 in the form of the convex seams 8 and the convex portions 68b on the peripheral surface reappear on the fibrous web 31 in the form of the concave seams 8. The concave portions 68a formed in the midsection of the peripheral surface correspond to the preset cutting lines 22 illustrated in (a) and (b) of FIG. 2 in a width direction. An imaginary line $C_2$ indicates a rotational center of the anvil 68.

In the ultrasonic processing apparatus 53 according to this invention, it is also possible to use the anvil as the first mechanical element and the horn as the second mechanical element. In this case, the anvil may be provided preferably in the form of a plate diagonally extending across the fibrous web 31 and the horn may be provided preferably in the form of a roller adapted to rotate and simultaneously to move forward diagonally across the fibrous web 31.

In the ultrasonic processing apparatus 53 according to this invention, it is also possible to use the anvil operating as the first mechanical element or the second mechanical element under a heated or cooled condition. When the anvil is used under a heated condition, the heating temperature may be set to an appropriate range, for example, of 70 to 80° C. In this case, even if the thermoplastic synthetic resin contained in the fibrous web 31 is fused by the ultrasonic processing and a portion of the thermoplastic synthetic resin forms small masses clinging to the anvil, such small masses should not be set under cooling effect and should not remain clinging to the anvil. The anvil under a heated condition may sometimes operate to provide an additional advantageous effect of reducing a time required for sealing of the fibrous web 31. When the anvil is used under cooled condition, the cooling temperature may be set to an appropriate range, for example, of 0 to −5° C. In this case, even if small masses of the thermoplastic synthetic resin as a result of the ultrasonic processing of the fibrous web 31, it is possible to cure such small mass quickly and to inhibit a possibility that the small mass might cling to the anvil.

While the ultrasonic processing apparatus is used to form the fibrous web 31 with the seams 8 in the exemplified embodiment, the applicable field is not limited thereto. The ultrasonic processing apparatus 53 according to this invention may be used also to cut the fibrous web 31 at predetermined regions using the horn 63 and/or the anvil 68 as fusing cutter blade(s) and at the same time to seal, along peripheral edges of the respective cut regions, the thermoplastic synthetic fibers or film made of thermoplastic synthetic resin or these fibers and film forming respective layers together of the fibrous web 31.

REFERENCE SIGNS LIST 31 fibrous web
51 conveying means on upstream side (conveying rolls)
52 conveying means on downstream side (conveying rolls)
63 horn
64 working surface
68 anvil
MD machine direction
CD cross direction

The invention claimed is:

1. An ultrasonic processing apparatus comprising an ultrasonic processing unit for subjecting a fibrous web to ultrasonic processing by interposing the fibrous web between a horn connected with an ultrasonic oscillator and an anvil opposed to the horn, wherein:

the ultrasonic processing apparatus includes upstream side conveying means and downstream side conveying means allowing the fibrous web to run in a machine direction continuously, between the upstream side conveying means and the downstream side conveying means, the ultrasonic processing unit including a first mechanical element defined by one of the horn and the anvil and a second mechanical element defined by a remainder is located in a face to face relation so that the fibrous web is nipped therebetween, the first mechanical element is a stationary element in the ultrasonic processing apparatus being movable neither in the machine direction nor in a cross direction with respect to the machine direction and having a working surface opposed to the second element, and the second mechanical element is a movable element adapted to rotate in the cross direction and at the same time to repeat back-and-forth movement between the machine direction and the cross direction across the fibrous web wherein, in the course of moving forward, the movable element is kept in contact with the fibrous web running in the machine direction and cooperates with the working surface of the first mechanical element to subject the fibrous web to the ultrasonic processing and, in the course of moving back, the movable element is spaced away from the fibrous web.

2. The ultrasonic processing apparatus defined by claim 1, wherein the working surface of the first mechanical element extends in parallel to the direction in which the second mechanical element repeats the back-and-forth movement.

3. The ultrasonic processing apparatus defined by claim 1, wherein the first mechanical element is defined by the horn and the second mechanical element is defined by a roller-like anvil.

4. The ultrasonic processing apparatus defined by claim 1, wherein the first mechanical element is defined by the anvil and the second mechanical element is defined by a roller-like horn.

5. The ultrasonic processing apparatus defined by claim 1, wherein the fibrous web comprises two or more fibrous webs interposed between the first mechanical element and the second mechanical element, and the first mechanical element and the second mechanical element are adapted to seal these two or more fibrous webs together.

6. The ultrasonic processing apparatus defined by claim 1, wherein the first mechanical element and the second mechanical element partially fuse and cut the fibrous web in a direction in which the second mechanical element repeats the back-and-forth movement.

7. The ultrasonic processing apparatus defined by claim 1, wherein the anvil is one of heatable type and coolable type.

8. The ultrasonic processing apparatus defined by claim 1, wherein the fibrous web comprises a web of contiguous diapers wherein the ultrasonic processing is applied to predetermined cutting lines of the web to be cut into individual diapers.

* * * * *